(12) United States Patent  
Salomon

(10) Patent No.: US 7,658,201 B2  
(45) Date of Patent: Feb. 9, 2010

(54) VALVE FOR STERILE SAMPLING OF A LIQUID SAMPLE FROM A CONTAINER

(75) Inventor: Henrik Lysgaard Salomon, Odense NV (DK)

(73) Assignee: Keofitt A/S, Odense NV (DK)

( * ) Notice: Subject to any disclaimer, the term of this patent is extended or adjusted under 35 U.S.C. 154(b) by 500 days.

(21) Appl. No.: 10/595,516

(22) PCT Filed: Oct. 28, 2004

(86) PCT No.: PCT/DK2004/000743

§ 371 (c)(1),
(2), (4) Date: Jun. 14, 2006

(87) PCT Pub. No.: WO2005/040671

PCT Pub. Date: May 6, 2005

(65) Prior Publication Data

US 2007/0074761 A1    Apr. 5, 2007

(30) Foreign Application Priority Data

Oct. 28, 2003    (DK) ................................ 2003 01586

(51) Int. Cl.  
*F16K 3/36* (2006.01)

(52) U.S. Cl. ............... 137/240; 137/625.48; 137/637.2; 137/606; 73/863.86

(58) Field of Classification Search ................. 137/240, 137/625.48, 625.5, 637, 637.2, 605, 606; 73/863.86

See application file for complete search history.

(56) References Cited

U.S. PATENT DOCUMENTS

| 4,836,236 | A | 6/1989 | Ladisch |
| 5,095,765 | A | 3/1992 | Filbey et al. |
| 5,246,204 | A | 9/1993 | Ottung |
| 6,056,003 | A | 5/2000 | Madsen et al. |
| 6,293,300 | B1 * | 9/2001 | Dumke et al. ............ 137/637.2 |
| 6,648,006 | B1 | 11/2003 | Ostergaard |
| 7,389,792 | B2 * | 6/2008 | Newberg .................... 137/240 |

FOREIGN PATENT DOCUMENTS

| DE | 19957306 | 12/2000 |
| DK | 174591 | 4/1992 |
| EP | 1 169 590 | 1/2002 |
| EP | 1 181 471 B1 | 2/2002 |
| SU | 838237 | 6/1981 |
| WO | 90/12972 A1 | 11/1990 |

* cited by examiner

Primary Examiner—Kevin L Lee  
(74) Attorney, Agent, or Firm—Sughrue Mion, PLLC

(57) ABSTRACT

A valve for sterile sampling of a liquid sample from a container includes a valve body (1) with a valve chamber (2). The valve includes a sample inlet (6) in the valve chamber (2), a first valve seat (7), a first valve plug (5a) for closing the sample inlet (6) through abutment against a first valve seat (7), an outlet (8) from the valve chamber (2), a cleaning inlet (9) in the valve chamber (2) for disinfection fluid, a second valve seat (10) and a second valve plug (5b). The outlet (8) is positioned between the two valve seats (7, 10), and the second valve seat (10) and the second valve plug (5b) are positioned in such a manner that the second valve plug (5b) through abutment against the second valve seat (10) cuts off the inflow of disinfection fluid in an area (2b) of the valve chamber (2) at the sample inlet (6).

12 Claims, 2 Drawing Sheets

VALVE FOR STERILE SAMPLING OF A LIQUID SAMPLE FROM A CONTAINER

BACKGROUND OF THE INVENTION

The present invention relates to a valve for sterile sampling of a liquid sample from a container, comprising a valve body with a valve chamber, a sample inlet in the valve chamber surrounded by a first valve seat, a first valve plug for closing the sample inlet through abutment against the first valve seat, an outlet from the valve chamber, a cleaning inlet in the valve chamber for disinfection fluid, a second valve seat and a second valve plug.

Valves of this type are among others used within the food industry for sampling samples of milk, juice, beer and the like, where there is a need for a sterile sealing valve for sampling of the samples. Such a sterile sealing is also advantageously used within for instance the pharmaceutical industry.

WO 90/12972 discloses a sampling valve with only a single valve seat. The valve seat is arranged around an axially disposed sample inlet, which is closed by displacement of a valve spindle, such that a valve spindle of rubber or a similar ductile material abuts against the valve seat. Moreover, the valve comprises an outlet, which in the mounted condition of the valve extends into the bore from below, and a cleaning inlet extending into the bore from above. As a consequence of this, the valve is adapted to be mounted in such a way in a container that its axis is substantially horizontal, for which reason the mounting of the valve can only take place with a very small degree of freedom. The cleaning inlet is connected with a source of sterilisation fluid through a sterilisation fluid valve.

In respect of this known valve sampling of a liquid sample typically involves the following steps:
1. Prior to cleaning/sterilisation and sampling the valve is in its closed condition, in which only the outlet and the cleaning inlet communicate with one another.
2. A sterilisation fluid is injected in the form of for instance vapour through the cleaning inlet.
3. The sterilisation fluid cleans the surfaces of the axial bore and the outlet, which have been in contact with a previously sampled liquid sample, if any, following which the sterilisation fluid leaves the valve body through the outlet.
4. The sample inlet is opened, whereby there is free communication between the sample inlet, the outlet and the cleaning inlet, and the contents of the container will, if the valve is correctly mounted, flow out of the outlet, following which it can be drawn in the form of a liquid sample.
5. The valve is closed again, following which it is ready for the next sterilisation and sampling.

At such a sampling it is quite common that an amount of container liquid flows into and at worst through the cleaning inlet. It is therefore necessary to arrange the sterilisation fluid valve for the source of the sterilisation fluid at a safe distance from the cleaning inlet in order not to contaminate the sterilisation fluid valve seat. This makes the sampling difficult, just as an undesirable cylinder clearance is created in the valve system, which in some cases is highly undesirable, as it results in considerable spillage.

DK 174591 discloses a sampling valve with a double valve seat and valve plug corresponding to the valve mentioned in the introduction. In this publication a first valve plug establishes by displacement of a first, interior valve spindle an interior, annular sealing surface against a first valve seat, whereas a second valve plug by displacement of a second, exterior valve spindle establishes an exterior, annular sealing surface against a second valve seat radially relative to the first annular sealing surface. Thus, two valve seats have been established radially relative to an axially disposed sample inlet. The purpose of establishing an additional valve seat is thus to improve the cleaning of the area, which in the closed condition of the valve is pinned between the sealing and the valve seat. This is done by a method substantially similar to the one disclosed in the above international application, but by alternating abutment of the two sealing membranes against the valve seats followed by a cleaning of the valve chamber. The valve according to this publication does not solve the aforementioned problems in respect of leakage of container liquid to the cleaning inlet.

SUMMARY OF THE INVENTION

The object of the present invention is on this background to provide a valve, which in order to avoid the above drawbacks prevents container liquid from flowing into and/or through the cleaning inlet. Another object of the invention is to provide a valve, which simplifies the sampling system and makes it more efficient, and which provides greater freedom of choice in respect of positioning the valve on the container.

In view of this, the valve according to the invention is characterized in that the outlet is positioned between the two valve seats and that the second valve seat and the second valve plug are positioned in such a manner that the second valve plug through abutment against the second valve seat cuts off the inflow of disinfection fluid in an area of the valve chamber at the outlet.

In this manner contamination of the cleaning inlet, the tube to the source of sterilisation fluid and/or the sterilisation fluid valve is completely avoided. This makes it possible to place the source of sterilisation fluid just after the cleaning inlet, as there is no risk of contaminating the sterilisation fluid valve seat. On the other hand the source of sterilisation fluid may be placed at liberty as to height, where it has hitherto often been necessary to place the source above the sterilisation fluid inlet to prevent backflow to the sterilisation fluid line. The sampling is therefore made easier, just as the described undesirable cylinder clearance in the system is avoided, and the spillage in the tube to the source of sterilisation fluid is prevented. As the inlet of sterilisation fluid takes place through a valve seat in the valve, the risk of airborne contamination of the sterilisation fluid inlet by disconnection of a sterilisation fluid tube is further eliminated.

Another considerable advantage in respect of the valve according to the invention is that in this valve a sterilisation fluid valve has been integrated, which simplifies the system, just as an external sterilisation fluid valve can be avoided, which is economically advantageous.

The valve according to the invention provides a complete freedom of choice in respect of the positioning of the valve. It may for instance be positioned at the bottom of a vessel, which in certain circumstances may be a considerable advantage.

According to an embodiment of the invention the valve chamber is formed by means of an axial bore, at one end of which the sample inlet is placed coaxially, the first valve plug is axially movable by displacement of a first valve spindle, which is coaxial to the bore, the second valve plug is annular and surrounds the first valve spindle, and the second valve plug defines through abutment against the second valve seat a cleaning chamber in the valve chamber. In this manner the disinfection fluid flows into the cleaning chamber, before it flows on in the valve chamber. The further flow in the valve chamber is thereby to a higher degree made axial and is directed directly towards the valve seat, the important cleaning of this area of the valve, which is accessible with difficulty, being improved. It is thus obtained that microorganisms present in the interspace, which can only be accessed with difficulty, just outside the valve seat between the valve plug and the wall of the valve chamber, are removed more effectively than would otherwise have been possible. Hereby, the risk at the sampling of contamination of the sample to be sampled from the container is reduced.

According to another embodiment a second, hollow valve spindle is provided, said spindle surrounding the first valve spindle, the first valve plug cuts off the sample inlet by displacement of the first valve spindle into abutment against the first valve seat, and the second valve plug cuts off the cleaning inlet by displacement of the second valve spindle into abutment against the second valve seat between the cleaning inlet and the outlet. In this manner a mutually independent, quick and easy opening and closing of the sample inlet and the cleaning inlet is obtained, the closing thereof being simultaneously safe and tight.

According to another embodiment the exterior of the valve plugs consists of a single flexible member, whereby a safe sealing between the spindle(s) and the valve chamber is obtained. The flexible member may advantageously comprise a bellows of a substantially not ductile material, whereby the life of the member is extended, just as the functionality and durability of the valve are improved.

In a preferred embodiment the outlet extends away from one end of the valve body from a mouth in the valve chamber, said mouth bordering the second valve seat, in which the sample inlet is placed.

BRIEF DESCRIPTION OF THE DRAWINGS

The invention will be explained in detail in the following by means of examples of embodiments with reference to the accompanying drawings, in which.

DETAILED DESCRIPTION OF THE INVENTION

Figure 1:
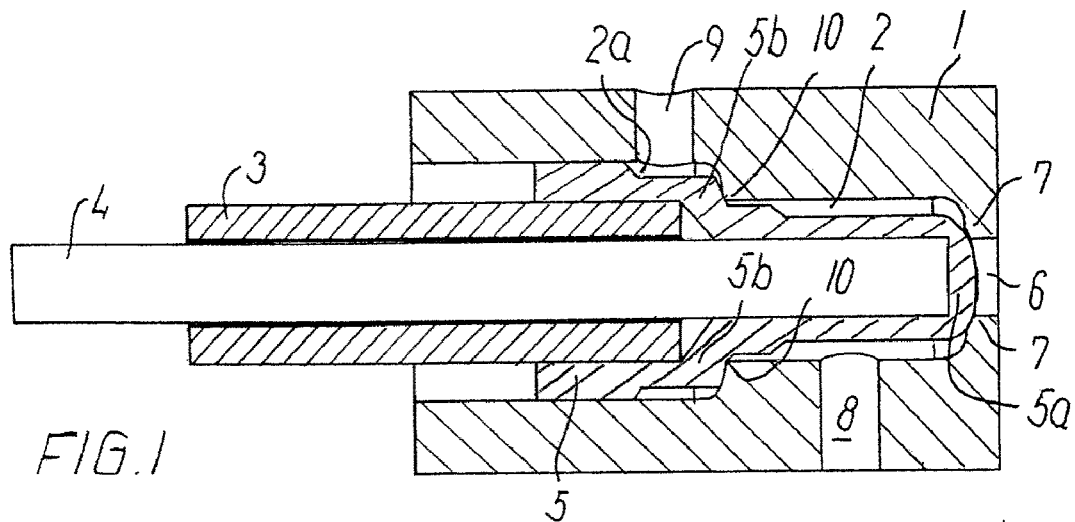
FIG. 1 is a sectional view of an embodiment of a valve according to the invention in a first condition, in which both the sample inlet and the cleaning inlet are closed.
Figure 2:
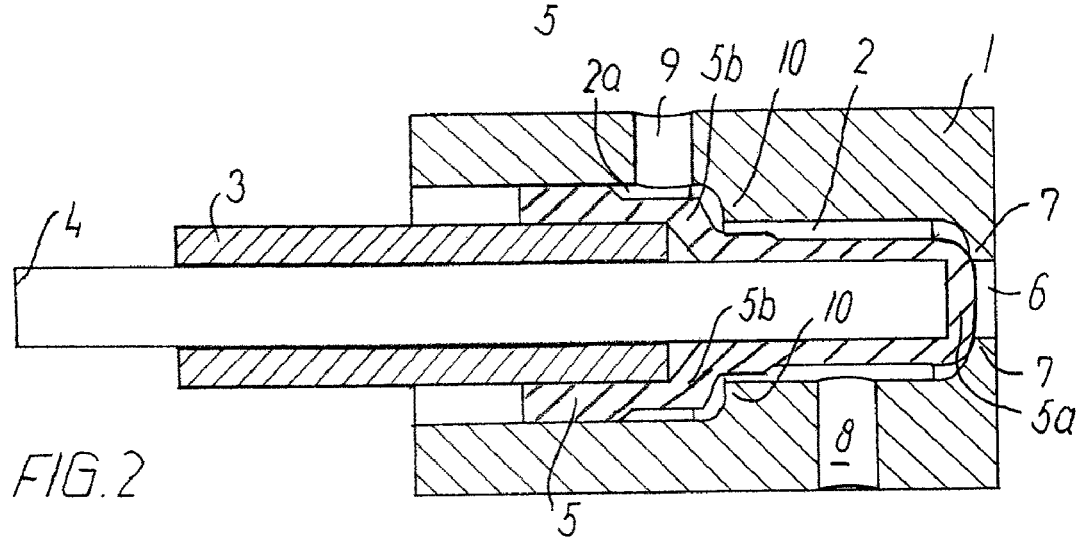
FIG. 2 is a sectional view of the valve in FIG. 1 in a second condition, in which the sample inlet is closed, whereas the cleaning inlet is open.
Figure 3:
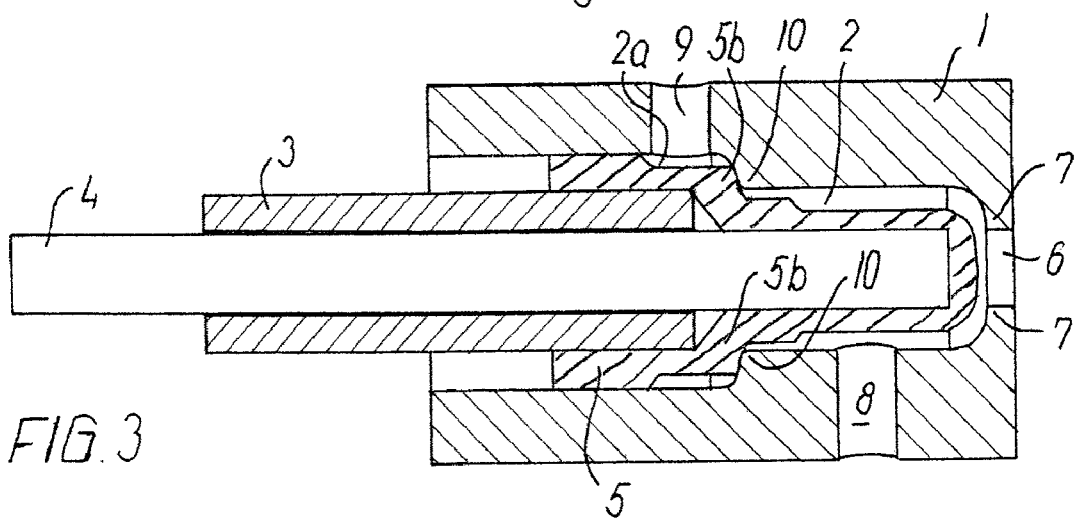
FIG. 3 is a sectional view of the valve in FIG. 1 in a third condition, in which the sample inlet is open, whereas the cleaning inlet is closed.

The embodiment shown in FIGS. 1 to 3 of the valve according to the invention comprises a valve body 1, in which a valve chamber is established in the form of an axial bore 2. In the bore 2 a hollow exterior valve spindle 3 has been axially arranged, in which spindle an inner valve spindle 4 is coaxially arranged. The valve. spindles 4, 3 are displaceable independently from each other in the axial direction of the valve. At the end of the valve spindles 4, 3 a first valve plug 5a and a second valve plug 5b are established in the form of areas of a single rubber case 5. The valve plugs 5a, 5b may, however, also be made of any suitable type of ductile material or a suitable not ductile material like PTFE (Teflon). In case of the latter the plugs may for instance comprise a bellows, which at the closing of the inlets 6, 9 may stretch like an accordion without stretching the material.

In the valve body 1 a sample inlet 6 has been provided coaxially with the valve, said inlet connecting the bore 2 with a container (not shown). Surrounding the sample inlet 6 a first annular valve seat 7 has been arranged. By displacement of the interior valve spindle 4 the first valve body 5a in the form of an area of the rubber case 5 presses against the first valve seat 7 in such a manner that the sample inlet 6 is cut off. In its open condition the sample inlet 6 communicates with the bore 2, which in turn communicates with an outlet 8 provided axially relative to the valve axis and in the valve body. A cleaning inlet 9 is furthermore established in the valve body, said inlet being connected with a source of disinfection fluid not shown. The cleaning inlet extends into a cleaning chamber 2a, which constitutes the exterior part of the bore 2. The cleaning chamber 2a is delimited from the rest of the bore 2 by a second valve seat 10. The cleaning chamber 2a is in the present description described as a part of the bore 2. The two bores/chambers may, however, also be viewed as separate bores/chambers.

The cleaning inlet 9 is displaced in the axial direction away from the sample inlet 6 relative to the outlet 8, such that the outlet 8 is placed between the two valve seats 7, 10. By a mutually independent axial movement of the exterior valve spindle 3 and the interior valve spindle 4 the sample inlet 6 and the cleaning inlet 9 can thus be opened and closed independently from each other. It is also possible to open and close the valve plugs 5a, 5b in other ways than by means of the valve spindles 3, 4 described. The second valve seat 10 may for instance be opened by application of a disinfection fluid pressure on the valve seat 10.

Figure 4:
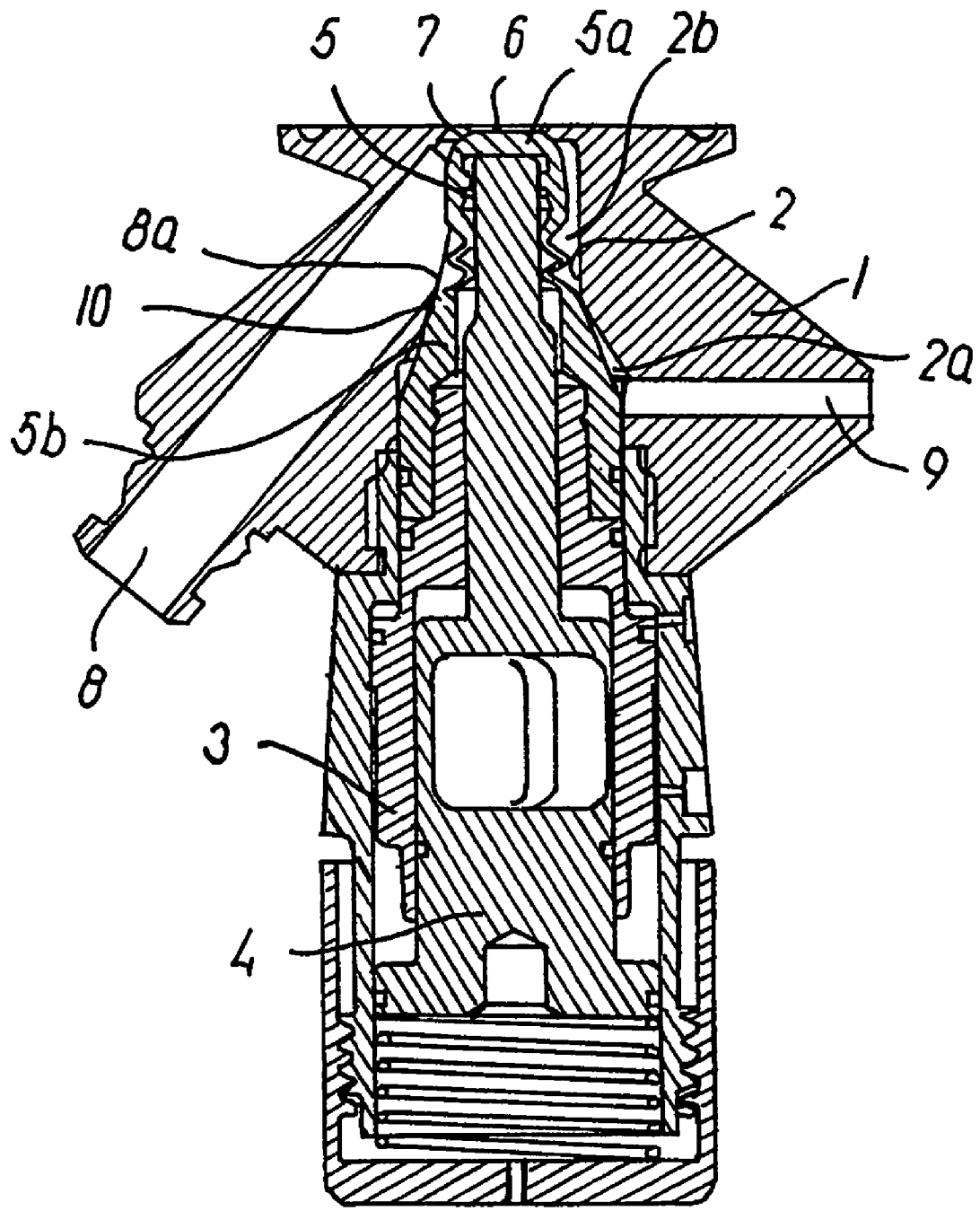
FIG. 4 is a sectional view of a preferred embodiment of a valve according to the invention.

FIG. 4 shows in greater detail a preferred embodiment of the invention. This embodiment generally comprises the same components as does the more schematically shown embodiment of FIGS. 1-3, and similar reference numerals have therefore been used for corresponding parts in FIGS. 1-3 and FIG. 4, respectively.

In the embodiment in FIG. 4 the outlet 8 is designed in such a way that by a vertical positioning of the valve, as shown in FIG. 4, the outlet 8 extends downwards from a mouth 8a in the bore 2. This mouth 8a borders on the second valve seat 10. The area 2b of the valve chamber or the bore 2 is therefore self-draining through the outlet 8, and it is possible to place the valve at the bottom of a container to use it as a drain-off valve. When used like this, the valve is, however, preferably tilted for instance 5° to ensure that liquid does not remain on the otherwise horizontal, annular area immediately above the second valve seat 10.

As a consequence of the particular construction a valve according to the invention may be placed on the container with far more freedom of choice than up till now.

Sampling of a liquid sample from the container with a valve according to the invention preferably takes place by means of the following steps.

1. Prior to sampling the valve is in the condition shown in FIG. 1, in which both the sample inlet and the cleaning inlet 9 are closed.
2. Only the disinfection fluid inlet 9 is opened through lifting of the exterior valve spindle 3, see FIG. 2. Hereby, the second valve plug 5b is lifted out of engagement with the second valve seat 10, such that a connection between the cleaning chamber 2a and the rest of the bore 2 is established.

3. Disinfection fluid in the form of for instance vapour fills the cleaning chamber 2a, following which the fluid continues into the remaining bore 2, directly towards the first valve seat 7.
4. The disinfection fluid inlet is closed through lowering of the exterior valve spindle 3, such that the valve is once more in the condition shown in FIG. 1.
5. Only the sample inlet 6 is opened through lifting of the interior valve spindle 4, see FIG. 3. Hereby, the first valve body 5a is lifted out of engagement with the first valve seat 7, such that container liquid flows into the bore 2 and out of the outlet 8, from where a liquid sample can be sampled.
6. The sample inlet is closed, such that the valve once more is in the condition shown in FIG. 1, following which the valve is ready for the next cleaning and sampling.

A more accurate sampling result is obtained by discarding the liquid sample sampled in step 5 and by repeating immediately hereafter the steps 1-6, the liquid sample taken for the second time in step 5 now being kept. Hereby, the area, which is pinned between the first valve plug 5a and the first valve seat 7, is rinsed before the final sample is sampled. In this area old container liquid from previous samplings may be present, and these remnants are removed by this method, such that the old remnants of liquid do not contaminate the last sample taken.

The invention is not limited to the embodiment described here. It is for instance possible within the scope of the patent claims to establish an inlet of disinfection fluid both through the cleaning chamber 2a and an inlet directly into the bore 2 corresponding to what is known from the above WO 90/12972.

The invention claimed is:

1. A sampling valve placeable on a container for sterile sampling of a liquid sample from the container, comprising:
   a valve body with a valve chamber;
   a sample inlet in the valve chamber surrounded by a first valve seat;
   a first valve plug inside the valve chamber for closing the sample inlet through abutment against the first valve seat;
   an outlet from the valve chamber;
   a cleaning inlet in the valve chamber for disinfection fluid; and
   a second valve seat and a second valve plug, the valve plugs being mutually independently moveable between opened and closed positions,
   wherein the outlet is positioned between the two valve seats, and the second valve seat and the second valve plug are positioned in such a manner that the second valve plug through abutment against the second valve seat cuts off the inflow of the disinfection fluid in an area of the valve chamber at the outlet.

2. A valve according to claim 1,
   wherein the valve chamber is formed by means of an axial bore, at one end of which the sample inlet is placed coaxially, the first valve plug is axially movable by displacement of a first valve spindle, which is coaxial to the bore, and the second valve plug is annular and surrounds the first valve spindle, and
   wherein the second valve plug through abutment against the second valve seat defines a cleaning chamber in the valve chamber.

3. A valve according to claim 2, further comprising a second, hollow valve spindle, said spindle surrounding the first valve spindle coaxially,
   wherein the first valve plug by displacement of the first valve spindle into abutment against the first valve seat cuts off the sample inlet, and
   wherein the second valve plug by displacement of the second valve spindle into abutment against the second valve seat cuts off the connection between the cleaning inlet and the outlet.

4. A valve according to claim 1, wherein the exterior of the valve plugs is formed by a single flexible member.

5. A valve according to claim 4, wherein the flexible member comprises a bellows of a substantially non ductile material.

6. A sampling valve placeable on a container for sterile sampling of a liquid sample from the container, comprising:
   a valve body with a valve chamber;
   a sample inlet in the valve chamber surrounded by a first valve seat;
   a first valve plug inside the valve chamber for closing the sample inlet through abutment against the first valve seat;
   an outlet from the valve chamber;
   a cleaning inlet in the valve chamber for disinfection fluid; and
   a second valve seat and a second valve plug, the valve plugs being mutually independently moveable between opened and closed positions,
   wherein the outlet is positioned between the two valve seats, and the second valve seat and the second valve plug are positioned in such a manner that the second valve plug through abutment against the second valve seat cuts off inflow of disinfection fluid in an area of the valve chamber at the outlet, and
   wherein the outlet from a mouth in the valve chamber, bordering on the second valve seat, extends away from an end of the valve body, in which the sample inlet is positioned.

7. A valve according to claim 6,
   wherein the valve chamber is formed by means of an axial bore, at one end of which the sample inlet is placed coaxially, the first valve plug is axially movable by displacement of a first valve spindle, which is coaxial to the bore, and the second valve plug is annular and surrounds the first valve spindle, and
   wherein the second valve plug through abutment against the second valve seat defines a cleaning chamber in the valve chamber.

8. A valve according to claim 7, further comprising a second, hollow valve spindle, said spindle surrounding the first valve spindle coaxially,
   wherein the first valve plug by displacement of the first valve spindle into abutment against the first valve seat cuts off the sample inlet, and
   wherein the second valve plug by displacement of the second valve spindle into abutment against the second valve seat cuts off the connection between the cleaning inlet and the outlet.

9. A valve according to claim 6, wherein the exterior of the valve plugs is formed by a single flexible member.

10. A valve according to claim 9, wherein the flexible member comprises a bellows of a substantially non ductile material.

11. A process of sampling through a valve placed on a container for sterile sampling of a liquid sample from the container, said sampling valve comprising a valve body with a valve chamber, a sample inlet in the valve chamber surrounded by a first valve seat, a first valve plug inside the valve chamber for closing the sample inlet through abutment against the first valve seat, an outlet from the valve chamber, a cleaning inlet in the valve chamber for disinfection fluid, a second valve seat and a second valve plug, the valve plugs being mutually independently moveable between opened and closed positions, wherein the outlet is positioned between the two valve seats, and the second valve seat and the second valve plug are positioned in such a manner that the second valve plug through abutment against the second valve seat cuts off inflow of disinfection fluid in an area of the valve chamber at the outlet, the process comprising the following steps:

connectiong the sample inlet with the container for sampling from said container;

connecting the cleaning inlet with a source of disinfection fluid; and raising the first and second valve plug in turn from their respective valve seats for allowing at one time a sample of liquid from the container to enter the area of the valve chamber at the outlet and exit the valve chamber through the outlet, and allowing at another time disinfection fluid to enter the area of the valve chamber at the outlet and exit the valve chamber through the outlet, respectively.

12. A process of sampling in accordance with claim 11, wherien the valve is provided with its outlet extending from a mouth in the valve chamber, bordering on the second valve seat, and extending away from an end of the valve body, in which the sample inlet is positioned.

* * * * *